United States Patent
Teo

(10) Patent No.: US 9,271,697 B2
(45) Date of Patent: Mar. 1, 2016

(54) ULTRASOUND IMAGING WITH SPECKLE SUPPRESSION VIA DIRECT RECTIFICATION OF SIGNALS

(75) Inventor: Tat-Jin Teo, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1673 days.

(21) Appl. No.: 12/053,088

(22) Filed: Mar. 21, 2008

(65) Prior Publication Data

US 2009/0240144 A1  Sep. 24, 2009

(51) Int. Cl.
*A61B 8/14* (2006.01)
*G01S 7/52* (2006.01)
*G01S 15/89* (2006.01)

(52) U.S. Cl.
CPC ............... *A61B 8/14* (2013.01); *G01S 7/52077* (2013.01); *G01S 15/8927* (2013.01)

(58) Field of Classification Search
USPC .......................... 600/437, 441, 447, 453, 463
See application file for complete search history.

(56) References Cited

U.S. PATENT DOCUMENTS

| 4,092,867 | A | * | 6/1978 | Matzuk | 73/609 |
| 4,488,434 | A | * | 12/1984 | O'Donnell | 73/602 |
| 4,561,019 | A | | 12/1985 | Lizzi et al. | |
| 4,608,868 | A | * | 9/1986 | Green | 73/606 |
| 4,771,470 | A | * | 9/1988 | Geiser et al. | 382/266 |

(Continued)

FOREIGN PATENT DOCUMENTS

DE   10027538   10/2001

OTHER PUBLICATIONS

K. Thangavel et al., Removal of Speckle Noise from Ultrasound Medical Image based on Special Filters: Comparative Study, Jun. 2009, ICGST-GVIP Journal, vol. 9, pp. 25-32.*

(Continued)

*Primary Examiner* — James Kish
*Assistant Examiner* — Serkan Akar
(74) *Attorney, Agent, or Firm* — Lowe Graham Jones PLLC; Bruce E. Black

(57) ABSTRACT

Described herein are systems and methods for suppressing speckle noise in ultrasound imaging. In an embodiment, speckle noise suppression is provided by incoherently summing echo waves that impinge the active aperture of the transducers. This incoherent summation prevents echo waves from destructively interfering and therefore prevents the signal 'nulls' that characterize speckle noise. In an exemplary embodiment, the incoherent summation is performed by subdividing a transducer into a plurality of smaller transducers and incoherently summing the electrical signals from the smaller transducers. In one exemplary embodiment, each of the smaller transducers is coupled to a separate rectifier, which rectifies the electrical signal from the respective transducer into a rectified signal. The rectified signals from the rectifiers are then summed to provide the incoherent summation.

16 Claims, 4 Drawing Sheets

(56) References Cited

U.S. PATENT DOCUMENTS

| | | | | |
|---|---|---|---|---|
| 4,837,578 | A * | 6/1989 | Gammell | 342/194 |
| 4,852,577 | A * | 8/1989 | Smith et al. | 600/443 |
| 5,331,964 | A * | 7/1994 | Trahey et al. | 600/447 |
| 5,445,150 | A * | 8/1995 | Dumoulin et al. | 600/424 |
| 5,477,858 | A * | 12/1995 | Norris et al. | 600/441 |
| 5,653,235 | A * | 8/1997 | Teo | 600/447 |
| 5,910,115 | A * | 6/1999 | Rigby | 600/443 |
| 5,961,461 | A * | 10/1999 | Mo et al. | 600/443 |
| 6,037,579 | A * | 3/2000 | Chan et al. | 250/216 |
| 6,071,240 | A * | 6/2000 | Hall et al. | 600/443 |
| 6,814,701 | B1 * | 11/2004 | Tamura | 600/443 |
| 2003/0103212 | A1 * | 6/2003 | Westphal et al. | 356/479 |
| 2005/0143640 | A1 * | 6/2005 | Hoctor et al. | 600/407 |
| 2006/0084875 | A1 * | 4/2006 | Knight | 600/462 |
| 2006/0173334 | A1 * | 8/2006 | Azuma et al. | 600/447 |
| 2008/0114239 | A1 * | 5/2008 | Randall et al. | 600/437 |
| 2008/0119421 | A1 * | 5/2008 | Tuszynski et al. | 514/34 |
| 2008/0128178 | A1 * | 6/2008 | Jia | 178/18.01 |
| 2009/0112089 | A1 * | 4/2009 | Barnard et al. | 600/443 |
| 2009/0240144 | A1 * | 9/2009 | Teo | 600/437 |

OTHER PUBLICATIONS

T. Ratha et al., A Modified Method for Speckle Noise Removal in Ultrasound Medical Images, Feb. 2010, Int. Journal of Comp. and Elec. Engineers, vol. 2, 54-58.*

S. Sudha, Speckle Noise Reduction in Ultrasound Images by Wavelet Tresholding based on Weighted Varience, Apr. 2009, Int. Journal of Comp. Theory and Eng., vol. 1, pp. 7-12.*

T. Koga, Speckle Noise Reduction and Edge-Enhancement of Coronary Plaque Tissue in IntravascularUltrasound Image by Using Anisotropic Diffusion Filter, 2008, Int. Journal of Circuits, Systems and Signal Processing, vol. 2, pp. 239-248.*

Fink, M. et al. "The Random Phase Transducer: A New Technique for Incoherent Processing—Basic Principles and Theory." IEEE Transactions on Ultrasonics, Ferroelectrics, and Frequency Control. vol. 37, No. 2, pp. 55-69 (1990).

* cited by examiner

ULTRASOUND IMAGING WITH SPECKLE SUPPRESSION VIA DIRECT RECTIFICATION OF SIGNALS

FIELD OF THE INVENTION

The present invention relates to ultrasound imaging, and more particularly to ultrasound imaging with speckle suppression.

BACKGROUND INFORMATION

Ultrasound imaging is used in the medical field to image inside a patient. Ultrasound imaging may be performed with an internal ultrasound imager received within the patient (e.g., intravascular ultrasound system) or an external ultrasound imager placed on the patient's skin. An ultrasound imager comprises one or more ultrasound transducers that emit ultrasonic waves into the patient. The ultrasound waves are reflected back to the transducer by layers of tissue or other structures in the patient as echo waves. A transducer converts received echo waves into electrical signals that are representative of the strength of the echo waves. The electrical signals are processed by an ultrasound image processor into an ultrasound image.

Current ultrasound transducers are coherent sensing devices that suffer from an imaging phenomenon known as speckle noise. Speckle noise is caused by the interference, both constructive and destructive, of echo wave fronts originating from scattering sources that are too small to be resolved by the transducer. A simple example of this is illustrated in FIGS. 1a and 1b. FIG. 1a shows an ultrasound wave 112 that is emitted from a transducer 110 and propagates towards a structure in the body, e.g., blood vessel wall 115. The ultrasound wave 112 is typically a periodic pressure wave having a frequency in the megahertz range. FIG. 1b shows an example of echo wave fronts 122a and 122b originating from two scattering sources 120a and 120b that are too small to be resolved by the transducer 110. The transducer 110 coherently sums the echo wave fronts 122a and 122b impinging on the active aperture of the transducer 110, and produces an electrical signal based on the coherent sum. If the echo wave front 122a impinges the transducer 110 at its peak and the echo wave front 122b impinges the transducer 110 at its trough, then the echo wave fronts 122a and 122b destructively interfere, and tend to cancel each other out. This destructive interference results in a dark spot in the ultrasound image at the blood vessel wall 115 even though the blood vessel wall 115 should appear bright in the image. Typically, scattering sources are distributed throughout the area of the body being imaged. The destructive interference of echo wave fronts originating from these scattering sources give rise to dark spots in the image that characterize speckle noise.

Speckle noise reduces the quality of the ultrasound image and, therefore, the ability of physicians and computers to perform diagnoses based on the image. Speckle noise is one reason many image processing algorithms, that work reasonably well for other imaging modalities such as CT or Magnetic Resonance (MR), do not work well for ultrasound images.

Therefore, there is a need in the art to suppress speckle noise in ultrasound imaging.

SUMMARY OF THE INVENTION

Described herein are systems and methods for suppressing speckle noise in ultrasound imaging.

In an embodiment, speckle noise suppression is provided by incoherently summing echo waves that impinge the active aperture of the transducers. This incoherent summation prevents echo waves from destructively interfering and therefore prevents the signal 'nulls' that characterize speckle noise.

In an exemplary embodiment, the incoherent summation is performed by sub-dividing a transducer into a plurality of smaller transducers and incoherently summing the electrical signals from the smaller transducers. In one exemplary embodiment, each of the smaller transducers is coupled to a separate rectifier, which rectifies the electrical signal from the respective transducer into a rectified signal. The rectified signals from the rectifiers are then summed to provide the incoherent summation.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

In order to better appreciate how the above-recited and other advantages and objects of the present inventions are objected, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION

Figure 1A:
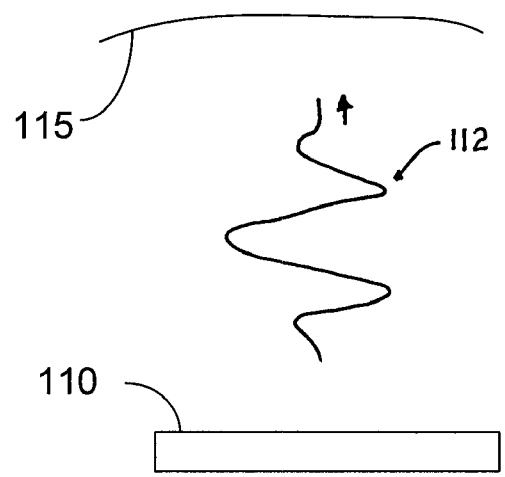
FIG. 1a shows an example in the prior art of an ultrasound wave emitted from a transducer.
Figure 1B:
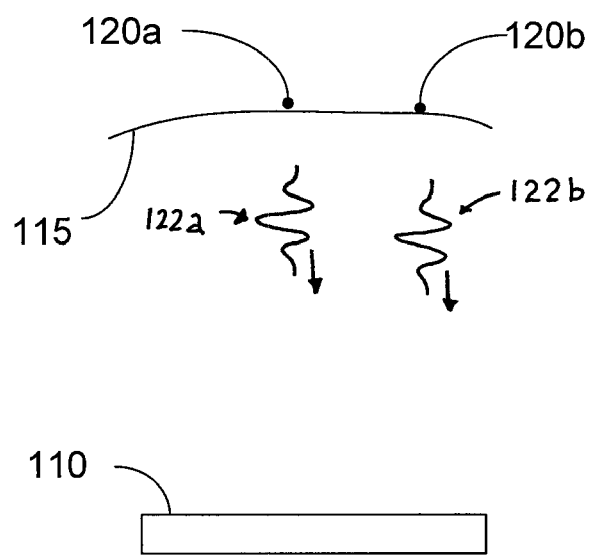
FIG. 1b shows an example in the prior art of two echo waves impinging on the transducer.
Figure 2:
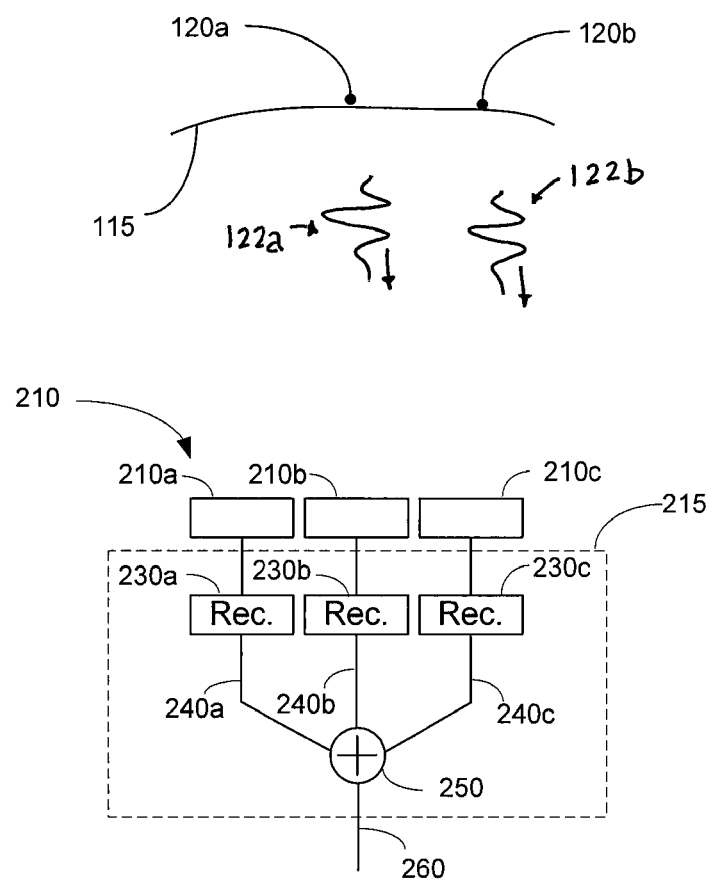
FIG. 2 shows a block diagram of a transducer and associated circuitry for suppressing speckle noise according to an exemplary embodiment of the present invention.

FIG. 2 shows a block diagram of a transducer 210 and receive circuitry 215 for suppressing speckle noise according to an embodiment of the present invention. In this embodiment, the transducer 210 is subdivided into a plurality of smaller transducers 210a-c. The transducers 210a-c subdivide the active transducer aperture into smaller areas, where each area corresponds to one of the transducers 210a-c. Each transducer 210a-c converts echo waves impinging on the transducer 210a-c into an electrical signal.

The receive circuitry 215 suppresses speckle noise by incoherently summing the electrical signals from the subdivided transducers 210a-210c. To do this, the receive circuitry 215 comprises a plurality of rectifiers 230a-c, where each rectifier 230a-230c is coupled to one of the transducers 210a-c. Each rectifier 230a-c rectifies the electrical signal from the corresponding transducer 210a-c into a rectified signal 240a-c so that only positive signals are obtained. The rectifiers 230a-c may be implemented using four-diode bridge rectifiers or other rectifying circuits known in the art. The rectified signals 240a-c are summed 250 into receive signal 260, which is sent to the ultrasound signal processor (not shown).

The electrical signals from the individual transducers 210a-210c are incoherently summed by rectifying each of the electrical signals with rectifiers 230a-c and summing the rectified signals 240 into receive signal 260. This incoherent summation suppresses speckle noise by preventing the destructive interference of echo waves that impinge on the active aperture of the transducer 210 and give rise to signal 'nulls' that characterize speckle noise.

The suppression of speckle noise can be demonstrated by way of example. FIG. 2 shows an example of echo wave fronts 122a and 122b originating from two scattering sources 120a and 120b. The echo wave 122a impinges transducer 210b and the echo wave 122b impinges transducer 210c. Unlike the prior art transducer 110, the echo waves 112a and 112b do not destructively interfere when the echo wave 122a impinges transducer 210b at its peak and the echo wave front 112b impinges transducer 210c at its trough. This is because the electrical signal from transducer 210c is rectified by rectifier 230c into a positive signal so that the electrical signals from transducers 210b and 210c add to each other instead of canceling each other.

The transducer 210 can be subdivided into any number of transducers 210a-c. The transducers 210a-c may be implemented using piezoelectric transducers. Alternatively, the transducers 210a-c may be implemented using capacitive micromachined ultrasonic transducers (CMUTs). An advantage of using CMUTs is that a large number of CMUTs can be fabricated on a single semiconductor substrate, e.g., silicon substrate, using known microfabrication techniques. CMUTs are typically much smaller than piezoelectric transducers (on the order of 10 to 100 microns in size). This allows the active transducer aperture to be subdivided into many small areas with each area corresponding to a single CMUT for improved speckle noise suppression. Another advantage of using CMUTs is that the rectifiers 230a-c can be fabricated on the same semiconductor substrate as the CMUTs using known integrated circuit (IC) techniques. For example, diodes can be fabricated on the semiconductor substrate to implement the rectifiers 230a-c. Alternatively, the rectifiers 230a-230c can be fabricated on a separate chip that is coupled to a CMUT chip, e.g., using a flip-chip arrangement, bonding wires, or the like.

A typical CMUT includes a drumhead structure suspended over a substrate in a manner to allow two-way conversion between a mechanical wave and an electrical signal through the modulation of a capacitive charge of the drum head. Further details on CMUTs can be found, for example, in U.S. patent application Ser. No. 10/966,594, titled "Integrated Bias Circuitry For Ultrasound Imaging Devices," filed on Oct. 14, 2004, the specification of which is incorporated herein by reference. The '594 application also describes bias circuitry that can be used to DC bias the CMUTs for optimal performance.

Figure 3A:
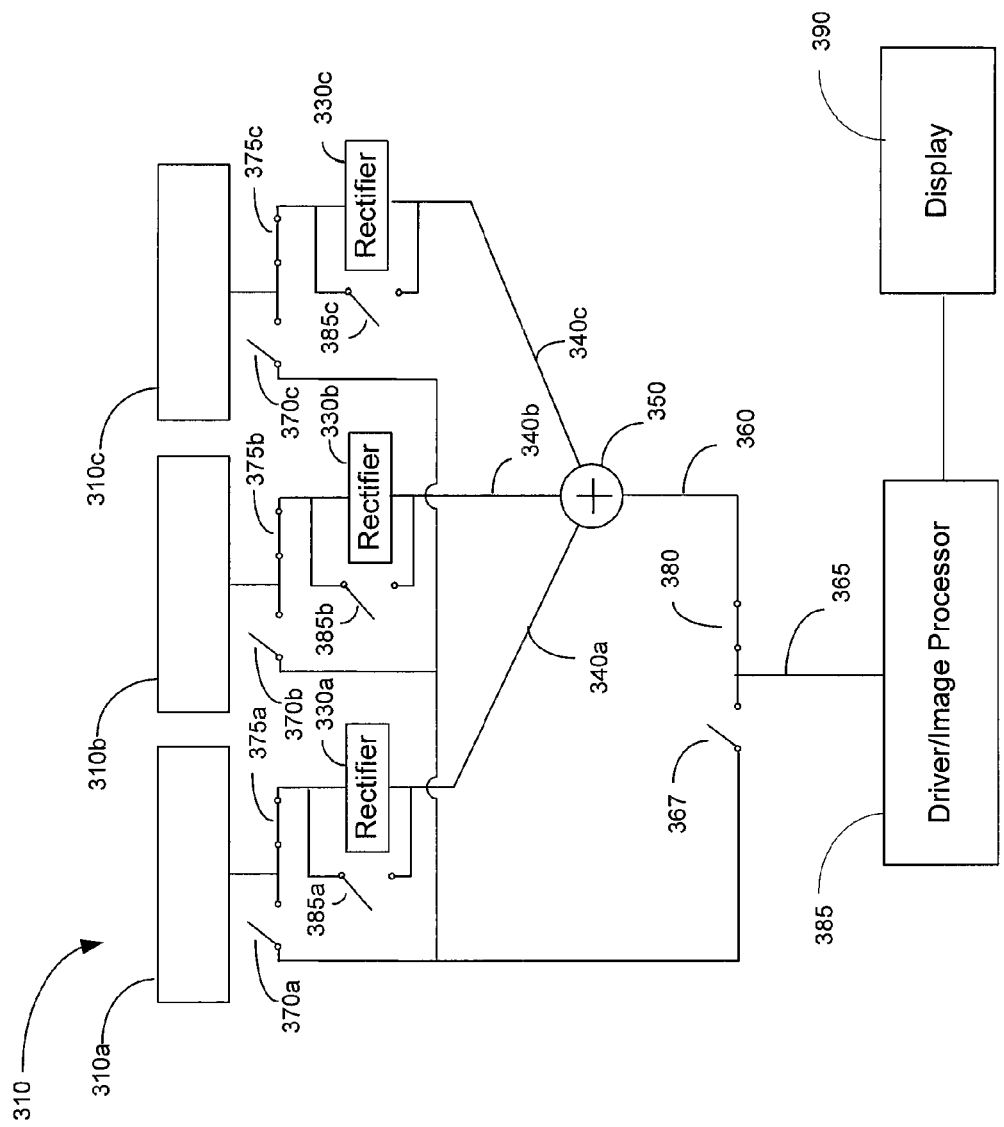
FIG. 3 shows a block diagram of a transducer and associated circuitry for suppressing speckle noise according to another exemplary embodiment of the present invention.

FIG. 3 shows a block diagram of a transducer 310 and circuitry for allowing the drive signal and the receive signal to be carried on a shared signal line 365 according to an embodiment of the present invention. The signal line 365 can be a coaxial cable, twisted pair wires, or the like. The signal line 365 is coupled at the other end to an ultrasound driver and signal processor 385.

In this embodiment, the transducer 310 is subdivided into a plurality of smaller transducers 310a-c, which subdivide the active transducer aperture into smaller areas. The circuitry comprises a plurality of switches 370a-c and 367 for coupling the drive signal from the signal line 360 to the transducers 310a-c. The switches 370a-c and 367 are closed when the transducers 310a-c are driven by the drive signal and are opened when the transducers 310a-c receive the resulting echo waves. The circuitry also comprises a plurality of switches 375a-c for selectively coupling the rectifiers 330a-c to the transducers 310a-310. The rectified signals 340a-c from the rectifiers 330a-c are summed 350 into receive signal 360. The circuitry further comprises a switch 380 for coupling the receive signal 360 to the signal line 365. The circuitry may include additional circuit components such as a preamplifier (not shown) for amplifying the receive signal. The receive signal 360 is sent to the image processor 385 where it is processed into an ultrasound image that is displayed on a display 390.

The circuitry may also comprise bypass switches 385a-c connected in parallel with the rectifiers 330a-c. When the bypass switches 385a-c are closed, the rectifiers 330a-c are bypassed, in which case the electrical signals from the transducers 310a-c are coherently summed. Thus, the bypass switches 385a-c allow the operator to switch the system between incoherent and incoherent imaging. The switches may be implemented using CMOS switches, electromechanical switches, or the like. An advantage of CMOS switches is that they can be fabricated on the same substrate as CMUTs using known IC fabrication techniques. The switches may be controlled by control logic (not shown) that is controlled by a control signal. The control signal can be carried on the shared signal line 365 or on a separate control signal line.

Figure 4:
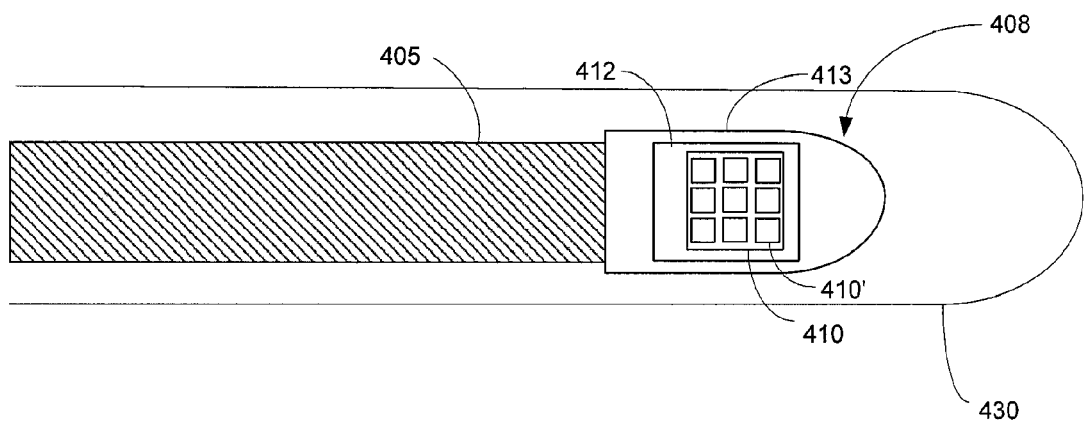
FIG. 4 shows a transducer for suppressing speckle noise mounted on the imaging core of a catheter according to exemplary embodiment of the present invention.

FIG. 4 shows a transducer 410 that is subdivided into smaller transducers 410' mounted on an imaging core 408 of an intravascular catheter according to an embodiment of the invention. Although the transducer 410 is subdivided into nine transducers 410' in the example shown in FIG. 4, the transducer 410 can be subdivided into any number of transducers in any arrangement. The imaging core 408 comprises a drive cable 405 and a distal housing 413 attached to the distal end of the drive cable 405. The transducer 410 is mounted in the distal housing 413 which has an opening 412 for the transducer 410. The imaging core 408 is slidably received within a catheter sheath 430 that is adapted to be inserted into a blood vessel of a patient. The drive cable 405 is used to rotate and translate the transducer 410 within the catheter sheath 20. The drive cable 405 may comprise two counterwound coils to provide a high torsional stiffness so that the drive cable 405 can transmit torque from a drive motor (not shown) to the transducer 410 while providing a low bending stiffness so that the drive cable 405 can bend along a tortuous path of a blood vessel. The transducer 410 is electrically coupled to the ultrasound system by an electrical cable or twisted pair wires running through a lumen in the drive cable 405. The transducer 410 is rotated by the drive cable 408 to scan a cross-sectional image of the blood vessel and moved longitudinally to image along a length of the blood vessel.

To suppress speckle noise using incoherent summation, the electrical signals from the subdivided transducers 410' are separately rectified and the rectified signals are summed into the receive signal. This may be accomplished using, e.g., the circuitry shown in FIGS. 2 and 3, where each transducer 410' is coupled to a separate rectifier. The circuitry may be integrated on a common substrate with the transducers 410' or on a separate chip placed within the distal housing 413.

Figure 5:
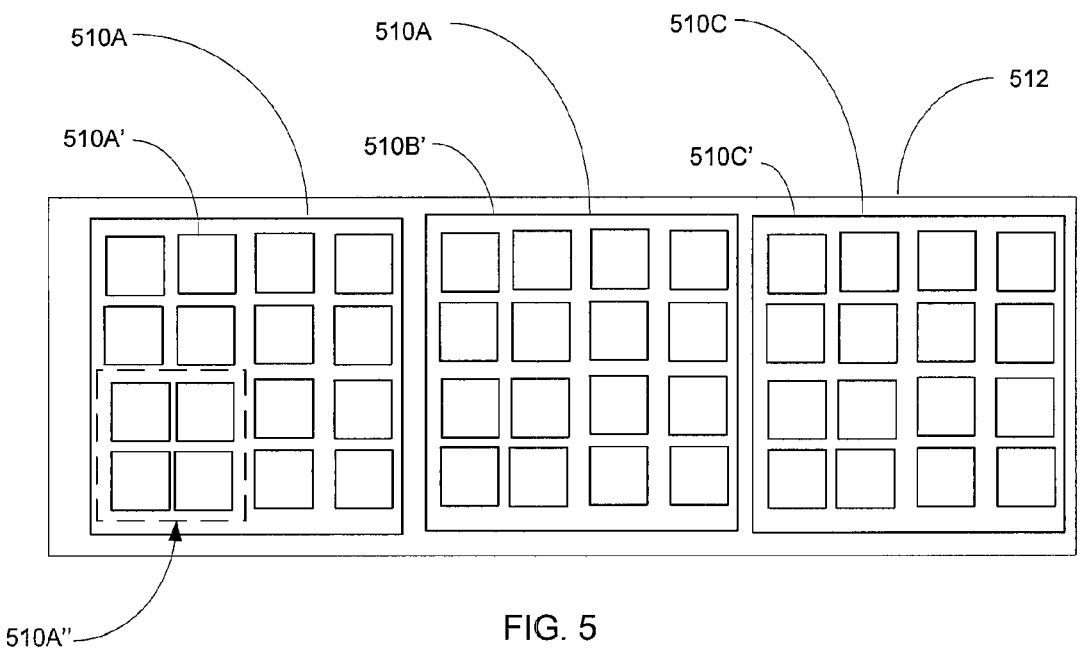
FIG. 5 shows a transducer array for suppressing speckle noise according to an exemplary embodiment of the present invention.

FIG. 5 shows an example of speckle noise suppression in an array of imaging elements 510A-C. Although the example in FIG. 5 shows a linear array of imaging elements, any number of imaging elements may be used in any arrangement such as a two-dimensional array, an annular array, or the like. In this example, each imaging element 510A-C is subdivided into small transducers 510A-C'. For each imaging element 510A-C, the electrical signals from the transducers 510A-C' within the imaging element 510A-C are incoherently summed to provide a receive signal for the respective imaging element 510A-C with reduced speckle noise. This may be accomplished by using, e.g., the circuitry shown in FIGS. 2 and 3 for each imaging element 510A-C. In the example shown in FIG. 5, each imaging element 510A-C comprises sixteen transducers 510A-C'. Thus, for each imaging element 510A-C, the electrical signals from sixteen transducers 510A-C' are incoherently summed to produce the receive signal for the imaging element 510A-C. The number of transducers 510A-C' whose electrical signals are incoherently summed may be dynamically changed instead of fixed. For example, instead of incoherently summing the electrical signals from all sixteen transducers 510N in imaging element 510A, the electrical signals from subsets of four transducers 510A" may be incoherently summed. In this case, four receive signals would be produced for imaging element 510A with each receive signal corresponding to the incoherent sum of four of the transducers 510A'. The dynamic change in the number of transducers used for incoherent summing can be implemented using additional summers and a switching network for selectively coupling the rectifiers to the summers.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions or a different combination or ordering of process actions. As a further example, each feature of one embodiment can be mixed and matched with other features shown in other embodiments. Additionally and obviously, features may be added or subtracted as desired. For example, the signals from the transducers may be inputted to a processor that is programmed to perform the rectification and summation. Accordingly, the invention is not to be restricted except in light of the attached claims and their equivalents.

What is claimed is:

1. A method for suppressing speckle noise in an imaging element comprising a plurality of transducers, comprising:
   incoherently summing electrical signals from the plurality of transducers into a receive signal consisting of the incoherently summed electrical signals; and
   generating an ultrasound image solely from the receive signal;
   wherein the incoherent summing comprises:
      rectifying the electrical signal from each transducer into a rectified signal; and
      directly summing, the rectified signals into the receive signal.

2. The method of claim of claim 1, further comprising rectifying the electrical signal from each transducer using a separate rectifying circuit.

3. An ultrasound imaging apparatus with speckle noise suppression, comprising:
   an imaging element comprising a plurality of transducers;
   a plurality of rectifiers, wherein each of the rectifiers is coupled to one of the transducers and is configured to rectify an electrical signal from the respective transducer into a rectified signal; and
   a summer directly coupled to the plurality of rectifiers to receive the rectified signal directly from the plurality of rectifiers, the summer configured to sum the rectified signals from the rectifiers into a receive signal consisting of the summed rectified signals.

4. The ultrasound imaging apparatus of claim 3, wherein the plurality of transducers comprise capacitive micromachined ultrasound transducer (CMUTs).

5. The ultrasound imaging apparatus of claim 4, wherein the transducers and rectifiers are integrated on a common substrate.

6. The ultrasound imaging apparatus of claim 3, wherein each rectifier comprises a diode bridge.

7. The ultrasound imaging apparatus of claim 3, further comprising an ultrasound imaging processor configured to process the receive signal into an ultrasound image.

8. The ultrasound imaging apparatus of claim 3, further comprising a plurality of bypass switches, wherein each bypass switch is coupled in parallel with one of the rectifiers to switch the imaging element between coherent imaging and incoherent imaging.

9. The ultrasound imaging apparatus of claim 3, further comprising a plurality of switches, where each switch is coupled between the one of the transducers and the respective rectifier for selectively coupling the transducer to the rectifier.

10. An ultrasound imaging apparatus with speckle noise suppression, comprising:
    an imaging element comprising a plurality of transducers;
    a plurality of rectifiers, wherein each of the rectifiers is coupled to one of the transducers and is configured to rectify an electrical signal from the respective transducer into a rectified signal; and
    a summer coupled to the plurality of rectifiers, the summer configured to receive the rectified signals from the rectifiers without intervening processing and to sum the rectified signals from the rectifiers into a receive signal.

11. The ultrasound imaging apparatus of claim 10, wherein the plurality of transducers comprise capacitive micromachined ultrasound transducer (CMUTs).

12. The ultrasound imaging apparatus of claim 11, wherein the transducers and rectifiers are integrated on a common substrate.

13. The ultrasound imaging apparatus of claim 10, wherein each rectifier comprises a diode bridge.

14. The ultrasound imaging apparatus of claim 10, further comprising an ultrasound imaging processor configured to process the receive signal into an ultrasound image.

15. The ultrasound imaging apparatus of claim 10, further comprising a plurality of bypass switches, wherein each bypass switch is coupled in parallel with one of the rectifiers to switch the imaging element between coherent imaging and incoherent imaging.

16. The ultrasound imaging apparatus of claim 10, further comprising a plurality of switches, where each switch is coupled between the one of the transducers and the respective rectifier for selectively coupling the transducer to the rectifier.

\* \* \* \* \*